United States Patent [19] [11] 4,152,786
Clark et al. [45] May 8, 1979

[54] COMPENSATOR FOR IMPLANTED BLOOD PUMP

[75] Inventors: Kenneth D. Clark, Pleasant Hill; Jal S. Jassawalla, San Francisco; Peer M. Portner, Berkeley, all of Calif.

[73] Assignee: Andros Incorporated, Berkeley, Calif.

[21] Appl. No.: 859,916

[22] Filed: Dec. 12, 1977

[51] Int. Cl.² ............................ A61F 1/24; A61M 1/03
[52] U.S. Cl. ............................................. 3/1.7; 138/30; 138/31
[58] Field of Search ..................... 3/1.7, 1; 128/1 D; 138/30, 31

[56] References Cited

U.S. PATENT DOCUMENTS

| 3,021,792 | 2/1962 | Johnson et al. | 92/94 X |
| 3,224,345 | 12/1965 | Doetsch | 138/30 X |
| 3,568,214 | 3/1971 | Goldschmied | 3/1.7 |
| 3,804,125 | 4/1974 | Sonneman | 138/30 |
| 3,860,968 | 1/1975 | Shapiro | 3/1.7 |
| 4,023,468 | 5/1977 | Poirier | 3/1.7 X |

Primary Examiner—Ronald L. Frinks
Attorney, Agent, or Firm—Fitch, Even & Tabin

[57] ABSTRACT

A compensator designed to be implanted within a living body and connected to an implanted reciprocating blood pump. A housing defines a gas-tight chamber which is separated into front and rear portions by a flexible membrane. A piston attached to the membrane guides the movement of the membrane, and a spring mechanism which links the piston and the housing is designed to maintain substantially constant pressure in the front chamber throughout the discharge and fill strokes of the reciprocating blood pump. Two pivoted, diametrically opposed, compression springs are compressed at rest at the end of the fill stroke and exert a force on the membrane which overcomes the differential pressure acting in the opposite direction when the membrane moves so as to expand the rear chamber volume.

8 Claims, 4 Drawing Figures

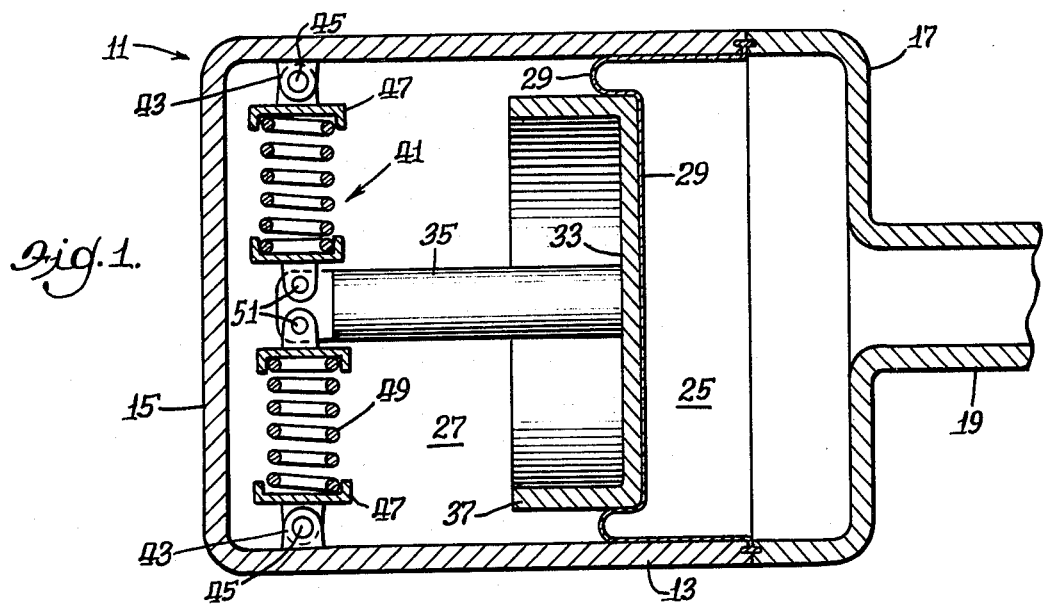
Fig. 1.
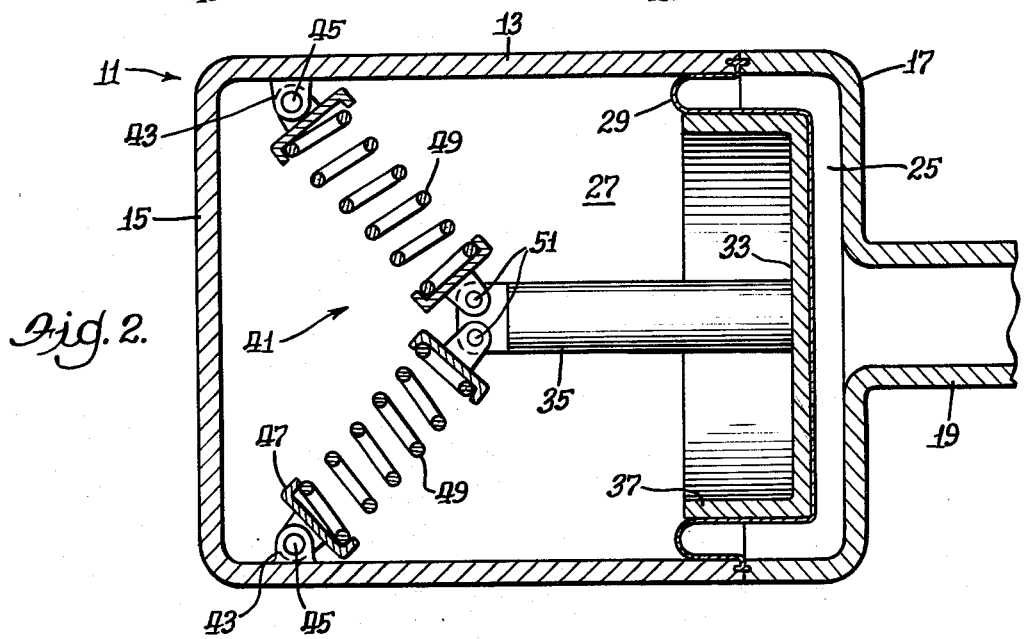
Fig. 2.
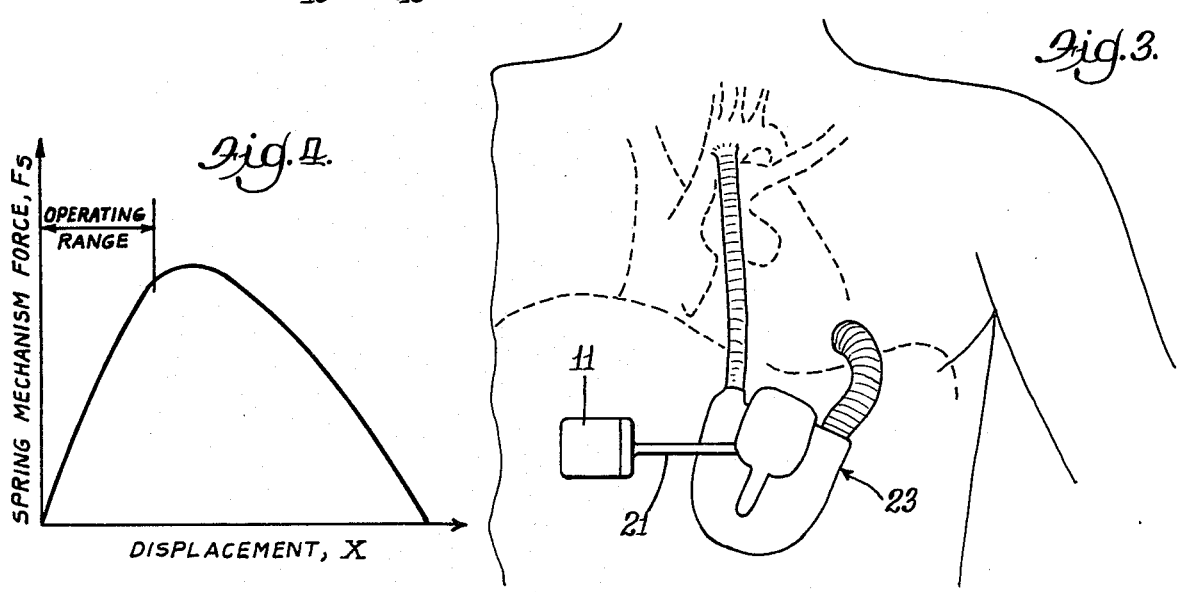
Fig. 3.
Fig. 4.

COMPENSATOR FOR IMPLANTED BLOOD PUMP

This invention relates to implantable heart assist devices and more particularly to a pressure-compensating accessory for use in conjunction with a reciprocating blood pump.

A reciprocating blood pump, as for example one which is designed as a left ventricular assist device, creates a variable volume as a result of its inherent reciprocating movement. If the rear or non-blood side of the pump is sealed off completely, the volume changes result in a large pressure fluctuation in the sealed-off space which impedes proper pump operation.

Various compensation schemes have been proposed for alleviating the undesired affects of such pressure fluctuations including, for example, percutaneous venting, saturated vapor compensation and flexible chamber walls. Percutaneous venting is considered to be the simplest technical solution; however, clinically, there are problems associated with possible vent obstrution, noise, as well as a potential for infection. While a saturated vapor compensation system appears feasible conceptually, it appears that the heat-transfer mechanism required to maintain saturated vapor at constant temperature during expansion and compression is difficult to achieve. The possibility of failure through fatigue has deterred the use of a flexible wall arrangement.

The present invention provides a constant pressure compensator which is designed to be small and compact in size, to compensate for the variable volume on the rear side of a reciprocating blood pump. The compensator uses a compression spring mechanism in combination with a flexible diaphragm to maintain a substantially constant pressure on the rear side of the pump to assure proper pump operation.

A thorough understanding of the invention will result from the following detailed description of a preferred embodiment of the invention when read in conjunction with the accompanying drawings wherein:

FIG. 1 is an enlarged sectional view showing a compensator in the operating position it assumes when the connected blood pump has just completed the fill or intake stroke;

FIG. 2 is a view similar to FIG. 1 showing the compensator in the position it assumes when the pump has just completed its discharge stroke;

FIG. 3 is a view, reduced in size, showing the compensator connected to a left ventricular assists blood pump; and FIG. 4 is a graph illustrating the spring force vs. the displacement.

The variable volume compensator includes a housing 11 having a generally circular cross section which is defned by a cylindrical sidewall 13 and which is closed by an integral rear wall 15. A front portion 17 of the housing is separately formed and provided with a tubular extension 19 which is connected by a pressure-resistant line 21 to a reciprocating circulation device or blood pump 23, which in the illustrated embodiment is a left ventricular assist blood pump. The connection of the line 21 is such that it is in fluid communication with the pump 23 at a location at the rear of the pump pusher plate which reciprocates to alternately fill a pumping chamber with blood and then discharge such blood.

The housing portions are made of a rigid material which is biocompatible, for example, a thick-walled polymeric material, such as a polycarbonate, or an appropriate metal, such as stainless steel or vitallium. The housing 11 may also be covered with a suitable coating to increase its biocompatibility. The housing 11 provides a gas-tight, rigid vessel which is divided into a front chamber 25 and a rear chamber 27 by a diaphragm 29. The diaphragm 29 is a flexible membrane of a type well known in the art and is generally circular in outline. The diaphragm may be made from a synthetic rubber or elastomeric material, such as that sold under the trademark Viton, and may be molded to the desired shape. Diaphragms of this general type have been used in diaphragm pumps for pumping various fluids as well as for creating vacuums. See for example, U.S. Pat. No. 3,021,792, issued Feb. 20, 1962, which discloses a fuel pump of the diapragm type.

The housing 11 is made in two pieces as illustrated, and the front portion 17 is suitably mated to the edge of the sidewall 13 of the main portion. The circular perimeter of the diaphragm 29 is suitably clamped between the two parts of the housing 11, as diagrammatically illustrated in the drawings.

The rear surface of the diaphragm 29 is attached to and reinforced by a piston 33 which has a circular front face that is disposed centrally of the membrane. The piston 33 includes a rearwardly extending rod portion 35 which terminates just short of the rear wall 15 of the housing. The piston may be attached to the rear surface of the diaphragm by cementing or by pinning or by any other suitable means, as is also well known in the art exemplified by the aforementioned patent. The piston 33 is preferably formed with a rearwardly extending skirt 37 which tends to guide the portion of the diaphragm that lies outward of the piston front face so that a rolling motion of the diaphragm is created during the motion of the piston (compare FIGS. 1 and 2). The diaphragm 29 itself will tend to stabilize the path of the front of the piston 33 during its movement and the rear end is linked to the housing as described hereinafter. However, if desired, some additional slide bearing arrangement (not shown) could be located generally in the location interior of the piston skirt 37 to assure smooth movement.

The extension tube portion 19 of the housing is in fluid communication with the rear side of the reciprocating blood pump 23. Accordingly, as the blood pump works on its discharge or pumping stroke, the space adjacent the rear side of the pumping pusher plate will increase in volume, thus tending to create a low pressure region in the extension tube and the front chamber 25 of the compensator. Oppositely, when the reciprocating pump 23 is working on the intake or fill stroke, the volume of this space will decrease and thus tend to create a higher pressure zone. These tendencies are compensated for by the movement of the diaphragm 29. It is the purpose of the compensator 11 to provide a diaphragm which moves forward and backward so as to maintain the pressure in the forward chamber 25 substantially constant, i.e., within about ±10 Torr. depending on the size of the housing. To accomplish this objective, the compensator 11 includes a spring mechanism 41 which produces a force which is substantially equal and opposite to the force resulting from the differential pressure which is created as a result of the movement of the pusher plate of the reciprocating blood pump 23.

The housing 11 is provided with a pair of inwardly extending and diametrically opposed ears 43 which are formed with a central aperture to receive a pivot pin 45.

Connected to the pivot pins 45 are the outward ends of a pair of spring retainers 47, and disposed in each of the spring retainers 47 is a compression spring 49. The inward ends of the spring retainers 47 are pivotally mounted by pins 51 to diametrically opposed locations on the piston rod 35 near the rear end thereof. The arrangement of the springs 49 is such that they guide the movement of the rear end of the piston rod 35 as it travels back and forth within the rear chamber 27.

In the position shown in FIG. 1, the compression springs 49 are loaded and are exerting a force. However, because the springs 49 are here coaxial and diametrically opposed, the forces exerted by both springs cancel each other out. As earlier indicated, when the piston 33 is in this rearward or withdrawn position, the blood pump 23 has just ended its fill stroke. Preferably, the construction of the device is such that, at this point in time, the pressure within both the rear chamber 27 and the front chamber 25 will be equal to each other and about one atmosphere.

As the pusher plate of the reciprocating blood pump 23 begins its discharge stroke, the volume of the space adjacent the rear side of the plate increases thus decreasing the pressure within the front chamber 25. As a result, the slightly higher pressure within the rear chamber 25 causes the diaphragm to begin to move to the right, as depicted in FIGS. 1 and 2. As soon as the spring mechanism 41 is offset from its dead-center or at-rest position shown in FIG. 1, the pair of compression spring 49 begin to exert a force in the direction (based upon the standard "xy" coordinates). The spring constant of the compression springs 49 is chosen to be such that the force applied by the uncoiling compression spring increases as they expand to substantially balance out the effect of the differential pressure resulting from the partial vacuum which is being created in the rear chamber 27. This is done by operating in the range wherein the springs have a negative spring constant. See for example FIG. 4. Accordingly, the piston 33 and the diaphragm 29 move smoothly to the right until the position as shown in FIG. 2 is reached. As a result, the pressure within the front chamber 25 remains substantially constant at about 1 atmosphere.

When the pumping stroke of the pusher plate of the blood pump 23 has ended and the fill or intake stroke begins, the pressure within the front chamber 25 will tend to increase and cause the diaphragm 29 and piston 33 to move back to the left. The original slight increase in pressure creates sufficient differential pressure relative to the substantially lower than atmospheric pressure in the expanded rear chamber 27 to overcome the force of the compression springs 49; and thus, the piston 33 moves to the left compressing the compression springs 49 until the atrest position is again reached that is depicted in FIG. 1. In this position, the pressure in the rear chamber 27 has returned to its original pressure, i.e., about 1 atmosphere, and throughout the intake stroke of the pump, the movement of the diaphragm 29 has caused the pressure in the forward chamber to remain very close to a constant value, i.e., 1 atmosphere. By optimizing the spring mechanism 41, it has been found that a net force approaching zero over the entire operating range can be achieved. By keeping the mass of the moving parts low, so as to minimize the dynamic inertial effects, it is believed that a net force on the piston 33 of ± about 5 Torr. can be obtained, in an overall housing 11 volume of about 150 cc., and thus a net pressure fluctuation of this magnitude in the pressure on the rear of the pump pusher plate.

It is believed that this compensator offers a compact, practical approach to the problem of variable volume that is created as a result of an implanted reciprocating blood pump. Because the housing is made of a rigid material, it can be encapsulated conventionally to provide biocompatibility, or as indicated hereinbefore, it can be made from a biocompatible, rigid material (e.g., titanium, stainless steel, vitallium, or polycarbonate). Moreover, because the flexible diaphragm 29 is totally encapsulated within the outer rigid housing 11, its biocompatibility does not come into consideration.

Although, preferably the pressures in the chambers 25 and 27 are equal, the compensator 11 could be biased to assist the filling stroke of the pump 23. This can be accomplished by setting the pressure in the rear chamber 27 so that there will always be a constant small force acting in the left-hand direction so as to assist the fill stroke of the blood pump. In such an instance, the pressure within the rear chamber 27 could be set slightly below 1 atmosphere, in the position as shown in FIG. 1, while the pressure in the front chamber is about 1 atmosphere.

Although the invention has been described with regard to a certain preferred embodiment, various changes and modifications as would be obvious to one having the ordinary skill in the art may be made without departing from the scope of the invention which is defined solely by the claims appended hereto.

Various of the features of the invention are set forth in the claims which follow.

What is claimed is:

1. A compensator designed for implantation within a living body in connection with an implanted reciprocating blood circulation device which compensator comprises
   a housing which defines a gas-tight chamber,
   a flexible membrane mounted in said housing which divides said chamber into a front portion and a gas-tight rear portion, said membrane being designed to permit movement to change the volume of said rear chamber portion,
   means for connecting said front portion in fluid communication with the reciprocating circulation device,
   compression spring means mounted in said rear portion, and
   means linking said spring means to said flexible membrane so that said compression spring means exerts a force against said membrane during the pumping stroke of said blood circulation device, which force assists in the movement of said membrane in a direction which causes the volume of said rear chamber portion to expand.

2. A compensator in accordance with claim 1 wherein said spring means comprises a pair of compression springs which are pivotally mounted to said housing in locations so as to be generally coaxial and opposed to each other at the end of the intake stroke of the reciprocating device when said rear chamber portion is at its least volume.

3. A compensator in accordance with claim 2 wherein piston means is connected to the rear surface of said flexible membrane and to each of said compression springs.

4. A compensator in accordance with claim 3 wherein each of said compression springs is pivotally connected to a rear location on said piston means with said pivot point being generally aligned with said common axis at the end of said intake stroke.

5. A compensator in accordance with claim 4 wherein both said springs are compressed at the end of said intake stroke and the force profile of said springs is such that the net force on said piston-membrane combination is not more than about ±5 Torr. when the volume of said housing is about 150 cc. or less.

6. A compensator in accordance with claim 1 wherein the pressure within said front and rear chamber portions is about equal at the end of the intake stroke.

7. A compensator in accordance with claim 1 wherein the pressure within said rear chamber is less than that within said front chamber portion at the end of the intake stroke so that said compensator assists the intake stroke of the reciprocating device.

8. A compensator in accordance with claim 1 wherein said spring means have a negative spring coefficient in their operating range.

* * * * *

UNITED STATES PATENT AND TRADEMARK OFFICE
CERTIFICATE OF CORRECTION

PATENT NO. : 4,152,786
DATED : May 8, 1979
INVENTOR(S) : Kenneth D. Clark; Jal S. Jassawalla; Peer M. Portner It is certified that error appears in the above-identified patent and that said Letters Patent are hereby corrected as shown below:

Column 1, line 22, change "obstrution" to --obstruction--.

Column 2, line 16; change "diapragm" to --diaphragm--.

Column 2, line 48, change "pumping" to --pump--.

Column 3, line 31, change "spring" to --springs--.

Column 3, line 35, change "spring" to --springs--.

Column 3, line 55, change "atrest" to --at-rest--.

Column 5, line 2, change "point" to --points--.

Signed and Sealed this

Sixteenth Day of October 1979

[SEAL]

Attest:

RUTH C. MASON
Attesting Officer

LUTRELLE F. PARKER
Acting Commissioner of Patents and Trademarks